United States Patent
Saxena et al.

(10) Patent No.: US 11,904,065 B2
(45) Date of Patent: Feb. 20, 2024

(54) APPARATUS AND METHOD FOR ULTRAVIOLET (UV) LIGHT SANITIZATION OF AN AIRCRAFT

(71) Applicant: HONEYWELL INTERNATIONAL INC., Morris Plains, NJ (US)

(72) Inventors: Sunit Kumar Saxena, Bangalore (IN); Stephen F. Yates, Des Plaines, IL (US)

(73) Assignee: HONEYWELL INTERNATIONAL INC., Charlotte, NC (US)

( * ) Notice: Subject to any disclaimer, the term of this patent is extended or adjusted under 35 U.S.C. 154(b) by 546 days.

(21) Appl. No.: 17/017,043

(22) Filed: Sep. 10, 2020

(65) Prior Publication Data

US 2022/0031897 A1 Feb. 3, 2022

(30) Foreign Application Priority Data

Jul. 29, 2020 (IN) .............................. 202011032458

(51) Int. Cl.
| | |
|---|---|
| A61L 2/10 | (2006.01) |
| A61L 2/26 | (2006.01) |
| B64F 5/30 | (2017.01) |
| B64D 45/00 | (2006.01) |

(52) U.S. Cl.
CPC .................. *A61L 2/26* (2013.01); *A61L 2/10* (2013.01); *B64D 45/00* (2013.01); *B64F 5/30* (2017.01); *A61L 2202/11* (2013.01); *A61L 2202/14* (2013.01); *A61L 2202/16* (2013.01); *A61L 2202/25* (2013.01)

(58) Field of Classification Search
CPC .............................. A61L 2/10; A61L 2202/16
See application file for complete search history.

(56) References Cited

U.S. PATENT DOCUMENTS

| | | | |
|---|---|---|---|
| 6,773,608 | B1 | 8/2004 | Hallett et al. |
| 8,859,994 | B2 | 10/2014 | Deal |
| 10,500,296 | B2 | 12/2019 | Kreitenberg |
| 10,583,212 | B2 | 3/2020 | Ufkes |

(Continued)

FOREIGN PATENT DOCUMENTS

| | | |
|---|---|---|
| IN | 111228527 A | 6/2020 |
| WO | 2015/116876 A1 | 8/2015 |

(Continued)

OTHER PUBLICATIONS

Purplesun, "Connected Software & Analytics," downloaded from https://www.purplesun.com/software/ on Sep. 10, 2020.

*Primary Examiner* — Kevin Joyner
(74) *Attorney, Agent, or Firm* — Lorenz & Kopf LLP

(57) ABSTRACT

Mobile apparatus and methods for ultraviolet (UV) light sanitization of an aircraft. The mobile apparatus generally comprises a mobile platform, such as a trolley, that has integrated therewith circuitry and devices that control and actuate ultra-violet C-spectrum (UV-C) light sources that are mechanically coupled to the trolley. The proposed mobile apparatus includes a controller that receives input from an operator and, optionally, from dosimeters mounted on the proposed system and/or within the aircraft. Based on the inputs received, the controller provides guidance to the operator in the form of alerts and messages, as well as automatically adjusting components of the mobile apparatus to adapt itself to a specific aircraft type.

14 Claims, 9 Drawing Sheets

(56) References Cited

U.S. PATENT DOCUMENTS

2013/0330235 A1\* 12/2013 Stibich ..................... A61L 2/24
                                                                422/292
2020/0085983 A1\*  3/2020 Ramanand ................ A61L 2/10

FOREIGN PATENT DOCUMENTS

| WO | 2018/042371 A1 | 4/2018 |
| WO | 2019/079982 A1 | 5/2019 |
| WO | 2019/143699 A9 | 7/2019 |

\* cited by examiner

APPARATUS AND METHOD FOR ULTRAVIOLET (UV) LIGHT SANITIZATION OF AN AIRCRAFT

CROSS REFERENCE TO RELATED APPLICATION

This application claims priority to Indian Provisional Patent Application No. 202011032458, filed Jul. 29, 2020, the entire content of which is incorporated by reference herein.

TECHNICAL FIELD

The technical field generally relates to sanitization systems, and more particularly relates to an apparatus and methods for ultraviolet (UV) light sanitization of an aircraft.

BACKGROUND

The sanitization of aircraft cabins is important for public health and safety. Recent events have increased demand for efficient and effective sanitization solutions. Some available solutions include using vertically mounted UV C-spectrum bulbs on an automated apparatus and using fixed wing trolleys within an aircraft cabin.

However, a technical problem is presented in that every aircraft cabin may provide a unique sanitization scenario. For example, seating configurations and aircraft cabin geometries can be aircraft-specific. In addition, a need for sanitization of an aircraft can be related to its recent use (e.g., a number of passengers, known health of passengers, and the like).

Therefore, technologically improved methods and apparatus for aircraft sanitization are desirable. Other desirable features and characteristics of the herein described embodiments will become apparent from the subsequent detailed description and the appended claims, taken in conjunction with the accompanying drawings and the foregoing technical field and background.

BRIEF SUMMARY

This summary is provided to describe select concepts in a simplified form that are further described in the Detailed Description. This summary is not intended to identify key or essential features of the claimed subject matter, nor is it intended to be used as an aid in determining the scope of the claimed subject matter.

In an embodiment, a mobile apparatus for ultraviolet (UV) light sanitization of an aircraft is provided. The mobile apparatus includes: a trolley, incorporating therewith a controller circuit operationally coupled to a motion sensor configured to detect directional motion of the trolley, and a user interface configured to receive operator input and provide visual feedback; a plurality of UV light sources, each UV light source configured to emit UV light outward from the trolley responsive to a respective radiation command of a respective plurality of radiation commands, each UV light source mechanically coupled via a respective actuator to the trolley, each actuator configured to affect an angular orientation of its UV light source responsive to a respective actuator command; the controller circuit configured to: receive from the user interface operator input that includes finalizing a seating configuration for the aircraft that is aircraft-specific; utilize the directional motion and the seating configuration to continuously determine a current location of the trolley with respect to the seating configuration; determine an optimal angular orientation of each UV light source of the plurality of UV light sources, as a function of the current location; and adaptively generate the plurality of radiation commands based on the current location, while the mobile apparatus is operated within the aircraft.

Also provided is a method for mobile ultraviolet (UV) light sanitization on an aircraft, including: coupling a plurality of UV C-spectrum (UVC) light sources to a trolley via respective actuators, each UVC light source configured to emit UVC light in response to a radiation command; configuring each of the UVC light sources to emit outward from the trolley with an emission angle controlled by its respective actuator in response to an actuator command; receiving, at a controller circuit, operator input finalizing a seating configuration for the aircraft; receiving, by the controller circuit, directional motion information for the trolley; continuously determining a current location of the trolley with respect to the seating configuration; determining an optimal angular orientation of each UV light source of the plurality of UV light sources, as a function of the current location; and adaptively generating, by the controller circuit, the radiation commands as a function of the current location of the trolley with respect to the seating configuration.

Furthermore, other desirable features and characteristics of the system and method will become apparent from the subsequent detailed description and the appended claims, taken in conjunction with the accompanying drawings and the preceding background.

BRIEF DESCRIPTION OF THE DRAWINGS

The present application will hereinafter be described in conjunction with the following drawing figures, wherein like numerals denote like elements, and.

DETAILED DESCRIPTION

Figure 1:
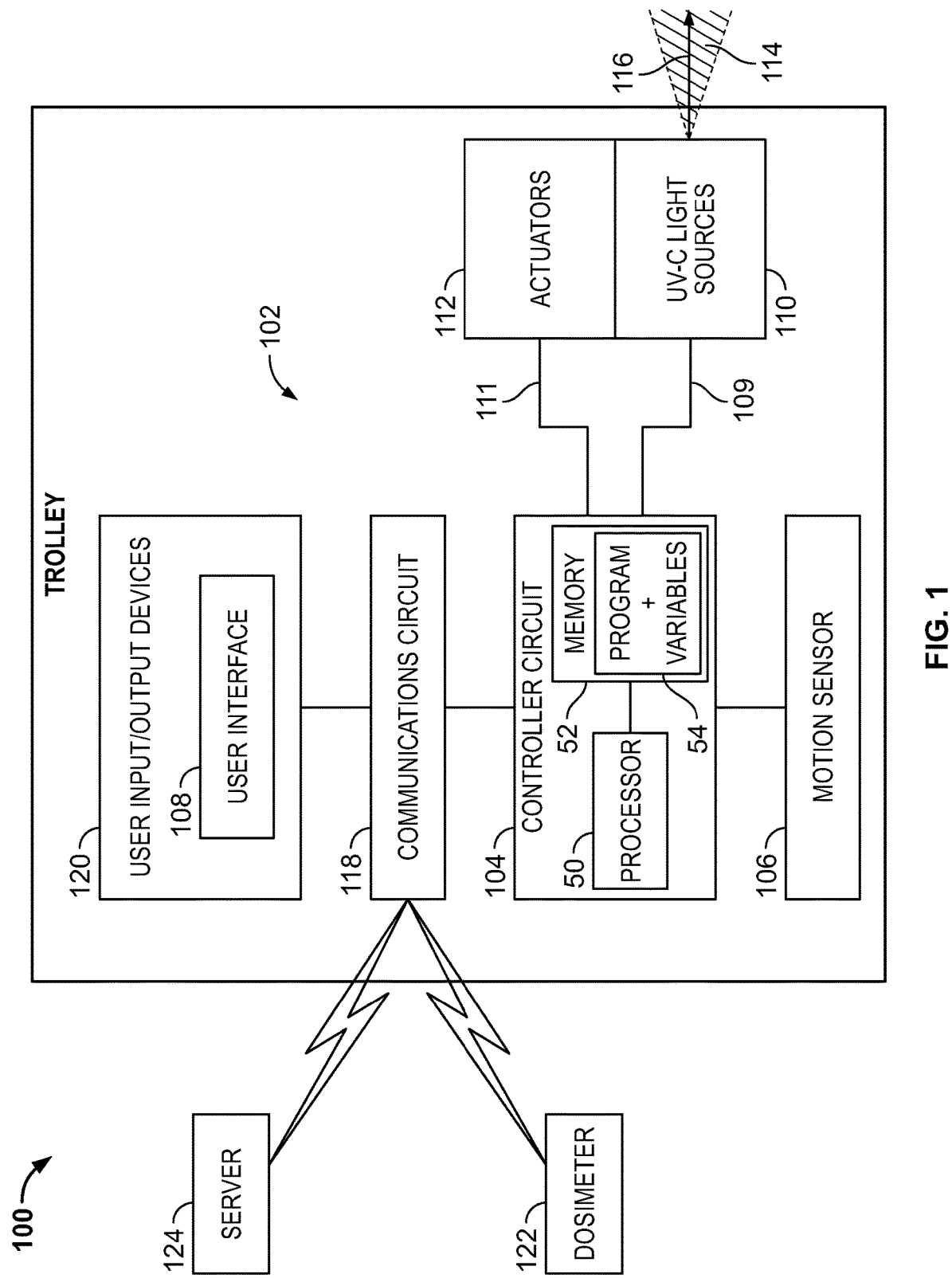
FIG. 1 is a diagram of a mobile apparatus for ultraviolet (UV) light sanitization of an aircraft, in accordance with an exemplary embodiment.

The following detailed description is merely illustrative in nature and is not intended to limit the embodiments of the subject matter or the application and uses of such embodiments. As used herein, the word "exemplary" means "serving as an example, instance, or illustration." Thus, any embodiment described herein as "exemplary" is not necessarily to be construed as preferred or advantageous over other embodiments. The embodiments described herein are exemplary embodiments provided to enable persons skilled in the art to make or use the invention and not to limit the scope of the invention that is defined by the claims. Furthermore, there is no intention to be bound by any expressed or implied theory presented in the preceding technical field, background, summary, or the following detailed description.

As mentioned, a technical problem is presented in aircraft sanitization in that every aircraft cabin may provide a unique sanitization scenario. Exemplary embodiments provide a technologically improved solution in the form of a mobile apparatus for ultraviolet (UV) light sanitization of an aircraft (also referred to herein as a "mobile apparatus"). The mobile apparatus generally comprises a mobile platform, such as a trolley, that has integrated therewith circuitry and devices that control and actuate ultra-violet C-spectrum (UV-C) light sources that are mechanically coupled to the trolley. The proposed mobile apparatus includes a controller that receives input from an operator and, optionally, from dosimeters mounted on the proposed system and/or within the aircraft. Based on the inputs received, the controller provides guidance to the operator in the form of alerts and messages, as well as automatically adjusting components of the mobile apparatus to adapt itself to a specific aircraft type.

Various embodiments of the mobile apparatus described herein additionally employ arms and actuators to automatically adjust the length of extension into a row of an aircraft seating configuration, the number of UV light sources employed, and an angular orientation of the UV light sources, in response to the inputs.

The proposed mobile apparatus may perform the following tasks:
  Automatically adjust the UVC radiation levels to meet aircraft-specific requirements for each aircraft, based on operator input and/or pre-programmed data.
  Utilize a start location to automatically keep track of the current position of the mobile apparatus with respect to the seating configuration and cabin geometry or layout.
  Utilize the current position of the mobile apparatus to provide specific instructions for the operator (i.e. "don't forget to open the lavatory door, go more slowly past certain seats, etc.).
  Warn the operator to slow down if the operator is going too fast (in a manual version of the system).
  Adjust the UV emission radiation level based on the feedback received from dosimeters installed at the target surfaces, and according to aircraft-specific requirements.
  Generate and transmit performance metrics to external servers Turning now to FIG. 1, the functional blocks of the mobile apparatus 102 are described in more detail. As used herein, the trolley 100 is at least a mobile frame to which the herein described elements are mechanically coupled to. In an embodiment, the trolley may take a form of a rectangular cart, with wheels for movement. However, in other embodiments, movement may be enabled without wheels, and the trolley shape may take various forms. The dimensions of the trolley 100 are limited by aircraft cabin geometry and are specifically sized to allow the trolley 100 to maneuver within the aisles of a seating configuration for an aircraft cabin. The mobile apparatus 102 is configured for use in a variety of different aircraft, and aircraft have different cabin geometries and different seating configurations. Therefore, the dimensions of the trolley 100 are selected to be slender enough to ensure a universal fit among a plurality of different aircraft, and specifically wide body aircraft and narrow body aircraft. Therefore, the dimensions of the trolley 100 are also short enough to have an acceptable turning ratio for operation inside a narrow body aircraft and a wide body aircraft.

A motion sensor 106 is configured to detect directional motion of the trolley 100. In some embodiments, the motion sensor 106 is a speedometer. A user interface 108 is configured to receive operator input and provide visual feedback. In various embodiments, the user interface 108 may embody one or more user input/output devices 120, and the one or more user input/output devices 120 may be integrated within the trolley 100. In an embodiment, the user interface 108 may be a graphical user interface (GUI) layout for a touchscreen display. In an embodiment, the user interface 108 may include one or more lightbulbs that light up, indicating an alert or operational status. In other embodiments, the user interface 108 may include commands and controls for any combination of: a keyboard, an alphanumeric display, and one or more lights that can be illuminated in different colors to provide the alerting described hereinbelow.

A plurality of UV light sources 110 are mechanically coupled to the trolley 100. Each UV light source 110 is configured to emit UV-C spectrum light 114 outward from at least one side of the trolley 100. The angular orientation or directionality of the UV-C spectrum light 114 from a given UV light source 110 may be described as along an axis 116 that is controlled by a respective actuator 112. Each UV light source 110 of the plurality of UV light sources 110 is configured to emit UV light outward from the trolley responsive to a respective radiation command 109 of a respective plurality of radiation commands 109. In an embodiment, the radiation commands 109 may be generated to selectively turn some of the UV light sources 110 on and some of them off to thereby achieve varying UVC emission intensity up and down, and this may change as a function of the current location of the trolley. In other embodiments, such as when the UV light source 110 is an LED, the radiation commands 109 may change a LED drive current or a duty cycle control to thereby achieve varying UVC emission intensity up and down. Accordingly, the emission of the UV-C spectrum light 114 is responsive to a respective radiation command 109, and that radiation command 109 may vary as function of current location and seating configuration.

Each UV light source 110 is mechanically coupled via a respective actuator 112 to the trolley 100. As mentioned, each actuator 112 is configured to affect an angular orientation of its respective UV light source 110 (e.g., the angular orientation of the axis 116 of the UV-C spectrum light 114) responsive to a respective actuator command 111. In some embodiments, each actuator 112 is configured to affect an angular orientation of its respective UV light source 110.

A controller circuit 104 is located on the trolley 100 and operationally coupled to the motion sensor 106 and the user interface 108. The controller circuit 104 performs the functions and operations of the mobile apparatus 102. In various embodiments, and as depicted in FIG. 1, the controller circuit 104 may be implemented as an enhanced computer system including a processor 50 configured by programming instructions (for example software program 54 and variables, stored in memory 52). In other embodiments, the controller circuit 104 may take the form of a programmable logic array, application specific circuit, or the like.

The processor 50 may comprise any type of processor or multiple processors, single integrated circuits such as a microprocessor, or any suitable number of integrated circuit devices and/or circuit boards working in cooperation to carry out the described operations, tasks, and functions by manipulating electrical signals representing data bits at memory locations in the system memory, as well as other processing of signals. The memory 52 may comprise RAM memory, ROM memory, flash memory, registers, a hard disk, or another suitable non-transitory short or long-term storage media capable of storing computer-executable programming instructions or other data for execution. The memory 52 may be located on and/or co-located on the same computer chip as the processor 50. Generally, the memory 52 maintains data bits and may be utilized by the processor 50 as storage and/or a scratch pad during operation. Specifically, the memory 52 stores instructions and applications. Information in the memory 52 may be organized and/or imported from an external data source during an initialization step of a process; it may also be programmed via a user input device.

A novel program 54 includes rules and instructions which, when executed, cause the processor 50 to perform the functions, techniques, and processing tasks associated with the operation of the mobile apparatus 102. Novel program 54 and associated stored variables may be stored in a functional form on computer readable media, as depicted, in memory 52. While the depicted exemplary embodiment is described in the context of a fully functioning enhanced computer system, those skilled in the art will recognize that the mechanisms of the present disclosure are capable of being distributed as a program product, with one or more types of non-transitory computer-readable signal bearing media used to store the program and the instructions thereof and carry out the distribution thereof, such as a non-transitory computer readable medium bearing the program 54 and containing computer instructions stored therein for causing a computer processor (such as the processor 50) to perform and execute the program 54. Such a program product may take a variety of forms, and the present disclosure applies equally regardless of the type of computer-readable signal bearing media used to carry out the distribution. Examples of signal bearing media include: recordable media such as floppy disks, hard drives, memory cards and optical disks, and transmission media such as digital and analog communication links. It will be appreciated that cloud-based storage and/or other techniques may also be utilized in certain embodiments.

During mobile apparatus 102 operation, the processor 50 may load and execute one or more programs, algorithms and rules embodied in the program 54, thereby being programmed with program 54. During execution of program 54, the processor 50 performs the processing activities of the mobile apparatus 102.

In various embodiments, the components of the mobile apparatus 102 may be communicatively coupled by any suitable physical or logical means of connecting computer systems and components, including, but not limited to, direct hard-wired connections, fiber optics, infrared and wireless bus technologies.

In various embodiments, a communications circuit 118 may be located on the trolley 100 and operationally coupled to the controller circuit 104. The communications circuit 118 is configured to support instantaneous (i.e., real time or current) communications between the mobile apparatus 102 and the one or more external data source(s), such as server 124. The communications circuit 118 may include one or more network interfaces and can be implemented using any suitable method and apparatus. As a functional block, the communications circuit 118 represents one or more transmitters, receivers, and the supporting communications hardware and software required for the mobile apparatus 102 to communicate with the various external data source(s) and user input/output devices 120 as described herein. In various embodiments, the communications circuit 118 may be configured to communicate with the operator by providing the visual feedback on the user interface 108 and receiving the operational instructions from the user interface 108.

In addition to informing the user, the controller may also report to a remote device the extent to which the operator has correctly operated the system, and the dose provided to each seat.; this is referred to as operational data and performance metrics. In various embodiments, the controller circuit 104 may be configured to generate the operational data and performance metrics, including at least a comparison of the logged emitted UV light as a function of the current location of the trolley to an aircraft-specific UV specification for the aircraft, and communicate the operational data and performance metrics to an external server 124 using the communications circuit 118. In this way a report can be provided to an aircraft owner or regulating body detailing the extent of disinfection by location in the aircraft cabin. This can allow remedial action to be taken if insufficient or excessive UV dose has been provided in specific locations.

In various embodiments, the communications circuit 118 may support communication with technicians, and/or one or more storage interfaces for direct connection to memory 52. Further, in various embodiments, the mobile apparatus 102 may utilize the communications circuit 118 to communicate with one or more dosimeters 122, distributed throughout the cabin of the aircraft.

Figure 2:
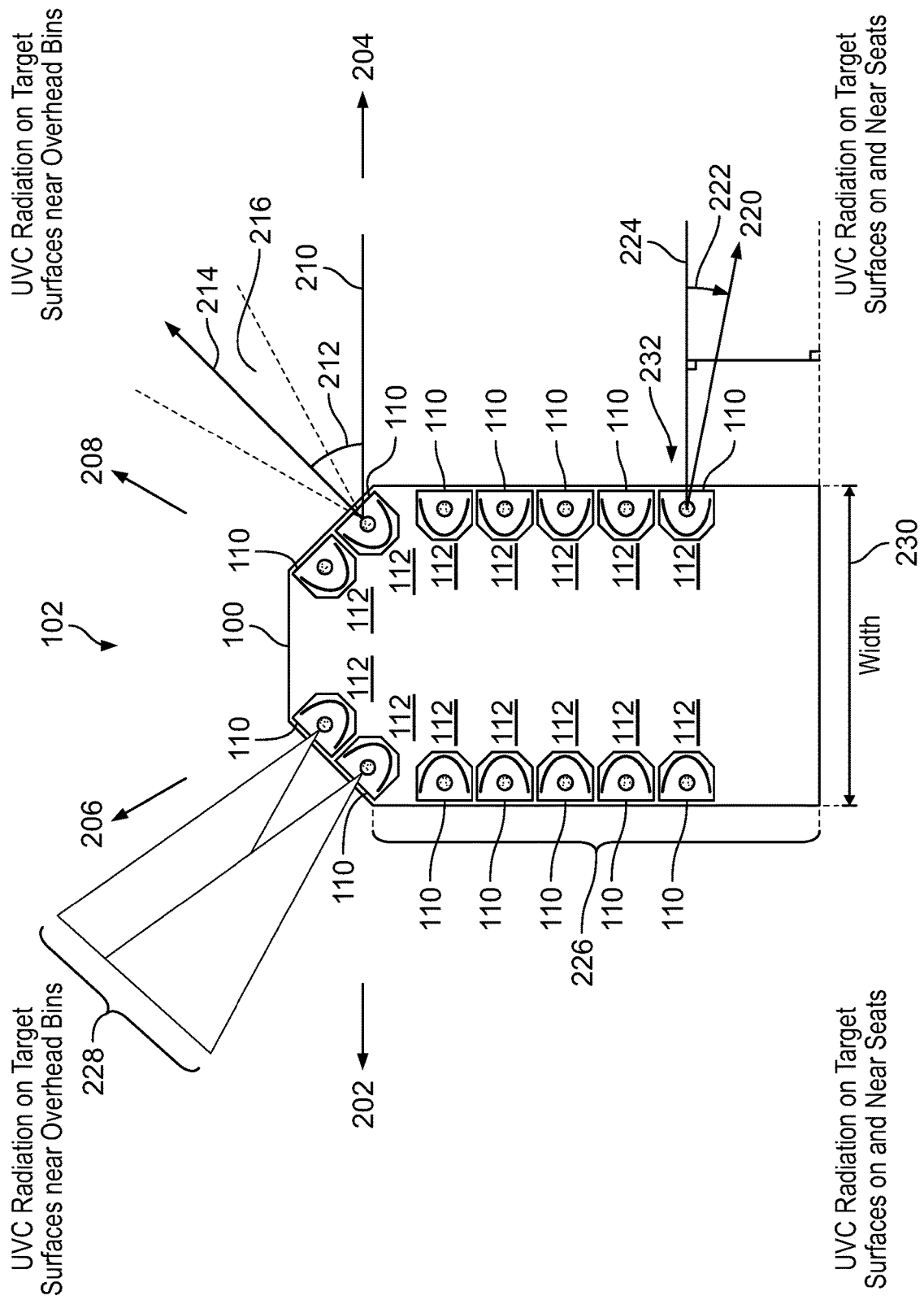
FIGS. 2-3 are two-dimensional illustrations of a mobile apparatus for ultraviolet (UV) light sanitization of an aircraft, in accordance with exemplary embodiments.
Figure 3:
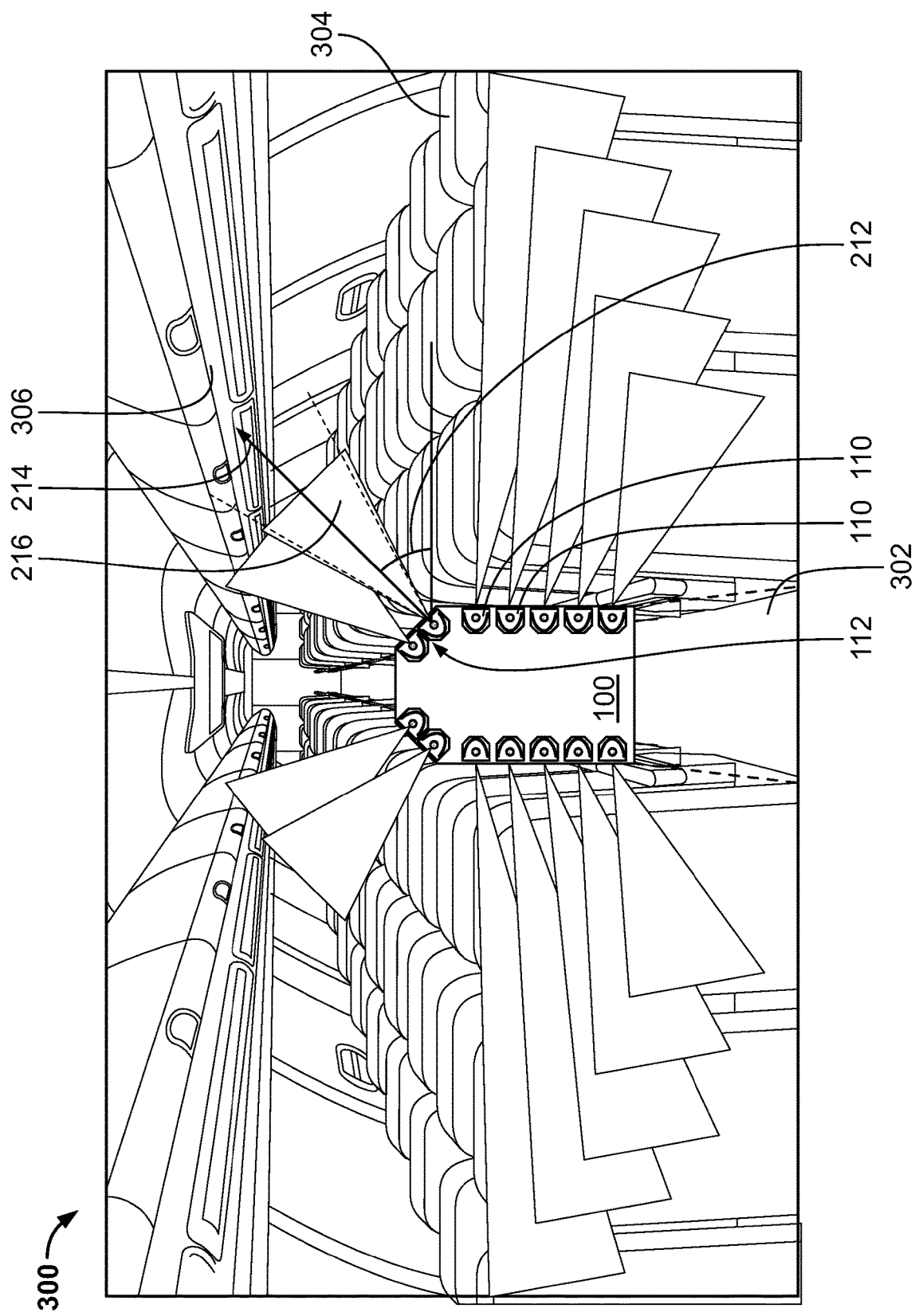

Turning now to FIGS. 2-3, and with continued reference to FIG. 1, a two-dimensional illustration of an embodiment of the mobile apparatus 102 is depicted with its bottom on the ground depicted by a dashed line near the bottom of the page. A plurality of UV light sources 110 are distributed along a left side of the trolley 100, with a first number of them stacked vertically in a region 226, emitting left 202, and a second number of them on a slanted surface emitting upward (arrow 206) in region 228. An area defined as the width 230 of the trolley 100 separates the left side from the right side. In various embodiments, the right side of the trolley is a mirror image of the left side. Lines 224 and 210 are parallel to ground. The UV light source 232 is representative of the UV light sources stacked vertically: it has an angle of radiation 222 of the axis 220 that is under the control of its respective actuator 112. The UV light source 234 is representative of the UV light sources on the slanted surface 208 (and as a mirror of those at 206) at the top of the trolley 100: it has an angle of radiation 212 of its axis 214 that is under the control of its respective actuator 112.

The previously described left side and right side of the trolley 100 are configured to be generally perpendicular to the rows of seats. FIG. 3 is a simplified illustration showing a side of the mobile apparatus 102 in an aisle 302 of an aircraft cabin 300. The depicted seating configuration has three seats 304 on each side of the aircraft cabin and has overhead bins 306 in an area generally understood to be an overhead compartment area, above the seats 304.

Figure 7:
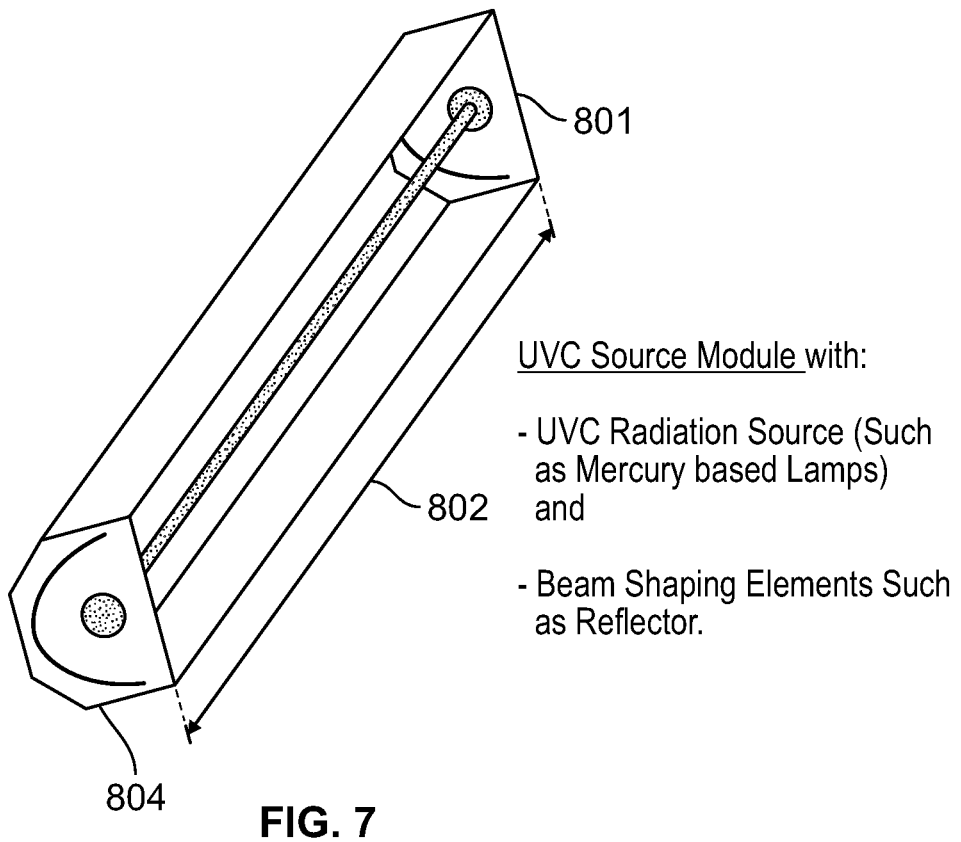
FIGS. 7-8 provide variations on a UV light source that may be used in a mobile apparatus for ultraviolet (UV) light sanitization of an aircraft, in accordance with exemplary embodiments.
Figure 8:
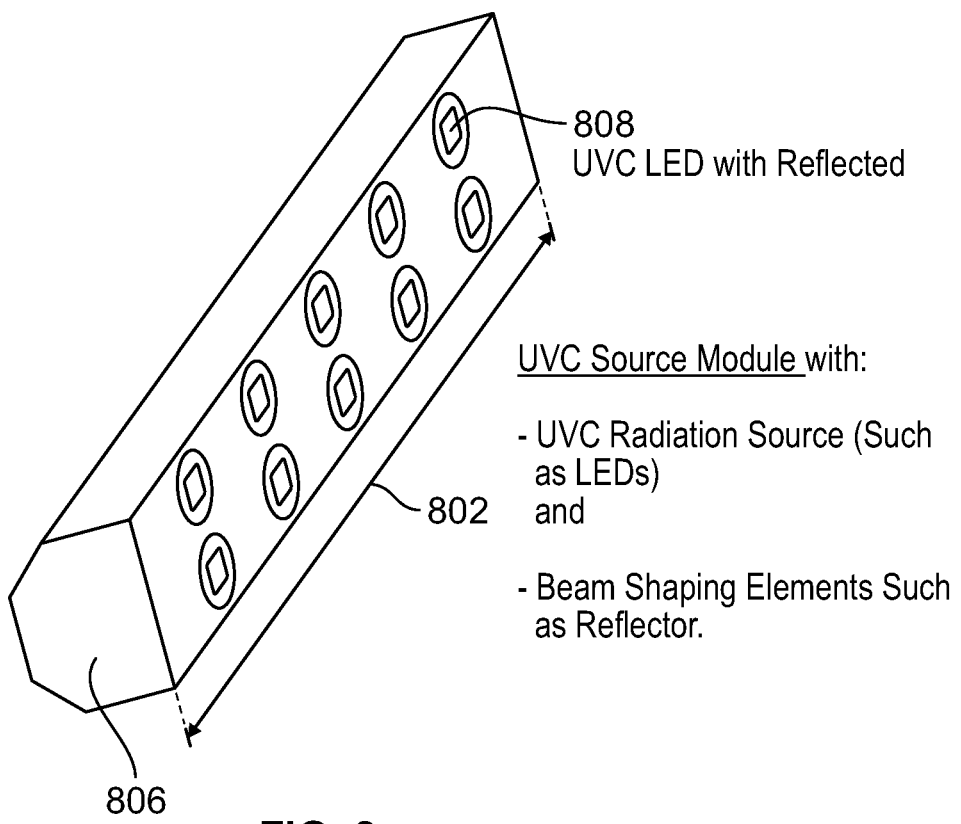

Although drawn in two-dimensions, one with skill in the art will appreciate that, in operation, the emitted light from the UV light sources 110 flare out into a three-dimensional space. To that end, looking forward to FIGS. 7-9, the UV light sources 110 are described in more detail. In a first embodiment, the UV light sources are each a UV-C spectrum (UVC) radiation source, such as a mercury-based lamp 801, horizontally mounted, having a length 802, and along the length 802 of the mercury-based lamp 801 is a beam shaping element, such as reflector 804. In FIG. 8, the UV light sources 806 are a UV-C spectrum (UVC) radiation source, such as a plurality of LEDs 808, each with a respective beam shaping element or reflector. Regardless of the embodiment of the UV light source 110, the controller circuit 104 may be further configured to reference a predefined radiation pattern to adaptively generate the respective radiation command 109 for each of the plurality of UV light sources 110. In various embodiments, the radiation pattern may be one of a plurality of pre-programmed radiation patterns, pre-programmed and stored in memory 52, for example. The plurality of radiation patterns may include variations in UV C-spectrum light intensity as a function of current location of the trolley with respect to the seating configuration. The plurality of radiation patterns may further include variations in UV C-spectrum light intensity as a function of a UV light source 110 location on the trolley (e.g., those in region 226 and those in region 228) and a current location of the trolley with respect to the seating configuration. Intensity variations may include a high, a medium, and a low intensity UV C-spectrum light. In various embodiments, the radiation pattern may further include pulsing or continuous radiation.

By enabling the variation of radiation patterns, and hence the optimization of UV radiation emitted in the aircraft cabin, the present invention provides a technological benefit. For each microorganism there exists a relationship between the percent disinfection and light dose (i.e. intensity x time). Higher dose will correspond to more complete disinfection. However, the higher the cumulative dose (over many treatments) the greater the impact on cabin furnishing like seat covers, wall coverings, seat belts etc. By optimizing the dose to that required for an individual location, we use enough UVC light to accomplish the required disinfection/sanitization, but not enough to prematurely damage aircraft components. Note also that intensity changes as the square of the distance from the light to the target. Therefore, intensity profiles will be specific to the arrangement of seats within the aircraft.

Figure 9:
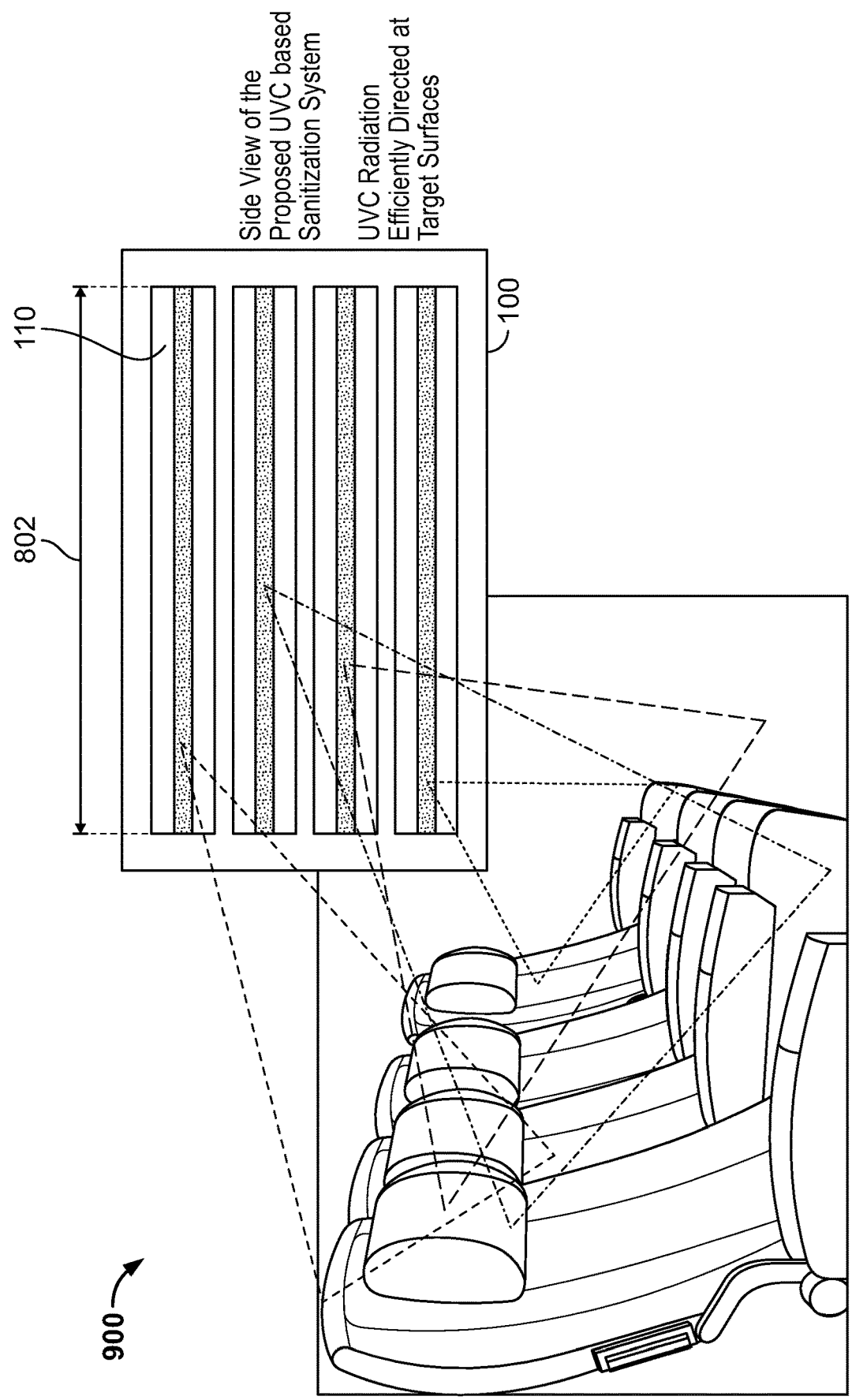
FIG. 9 is a simplified illustration of a side view of a mobile apparatus for ultraviolet (UV) light sanitization of an aircraft, shown among seats in a seating configuration of an aircraft.

The length 802 is reflective of horizontally mounted UVC bulbs and related to a depth of the trolley 100 that is not visible in the previously described two-dimensional illustrations but is generally addressed in FIG. 9. UV light is emitted along the length 802 of a given UV light source 110. FIG. 9 provides an illustration of a row in an aircraft cabin 900 and a simplified side view of the trolley 100 of the mobile apparatus 102.

Figure 4:
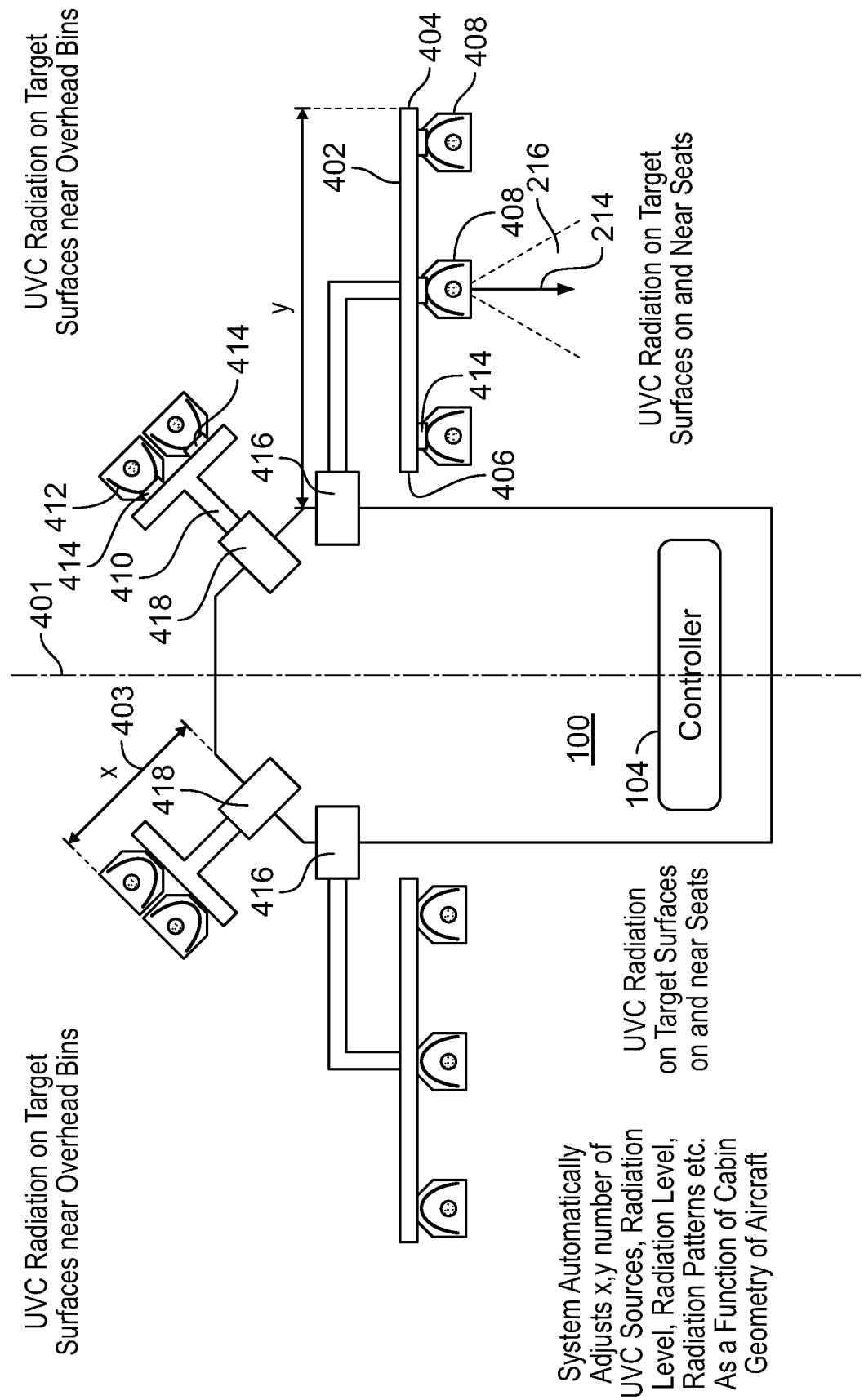
FIGS. 4-5 are two-dimensional illustrations of a variation of a mobile apparatus for ultraviolet (UV) light sanitization of an aircraft, in accordance with exemplary embodiments.

Returning now to FIGS. 4-6, some variations on the mobile apparatus 102 are illustrated and described. As mentioned, the UV light sources 110 may be mechanically coupled via a respective actuator 112 to the trolley 100. In an embodiment, at least some of the actuators 112, and hence, the respective UV light sources 110, are further mechanically coupled to an extension arm 402. The extension arm 402 is mechanically coupled to the trolley 100. The extension arm 402 has a proximal end 406 and a distal end 404, and at least one extension UV light source 408 is installed between the distal end 404 and the proximal end 406. The extension arm 402 comprises an extension actuator 416 that is responsive to an extension actuator command from the controller circuit 104. The extension actuator 416 moves or extends the extension arm 402 forward and back with respect to the core 401 of the trolley 100, such that the distal end 404 can be positioned up to a distance Y from a side of the trolley 100.

In an embodiment, an overhead arm 410 may be coupled to the trolley 100. The overhead arm 410 comprises at least one overhead UV light source 412. The overhead arm 410 comprises an overhead actuator 418 that is responsive to an overhead actuator command from the controller circuit 104. The overhead actuator 418 extends the at least one overhead UV light source 412 up to a distance X away from the surface 403 of the trolley Note that surface 403 is roughly analogous to region 228, having a slant toward an overhead compartment area of the aircraft cabin.

Figure 5:
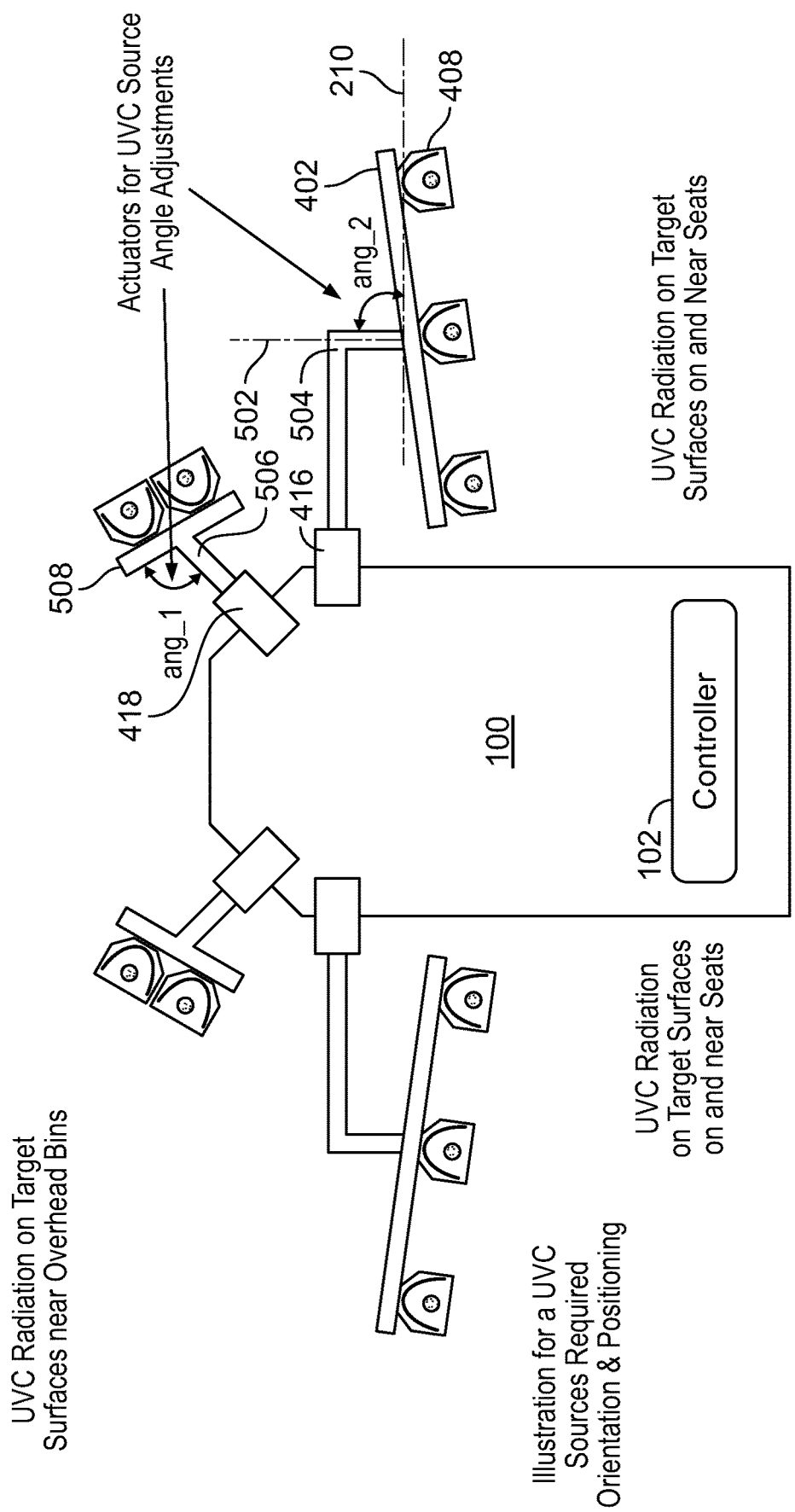

In addition to extending, each of the extension arm 402 and overhead arm 410 may articulate to change angles. An actuator 504 may change an angle (ang_2) with respect to ground of the UV Light sources 408 distributed on the extension arm 402. Line 502 is perpendicular to line 210, which was introduced as being parallel to ground. In FIG. 5, actuator 504 changes ang_2, it is less than or equal to ninety degrees from line 502 in the figure. Similarly, actuator 506 can change an angle (ang_1) of a platform 508 with respect to the overhead arm 410; the platform 508 having one or more UV Light sources 412 thereon.

Figure 6:
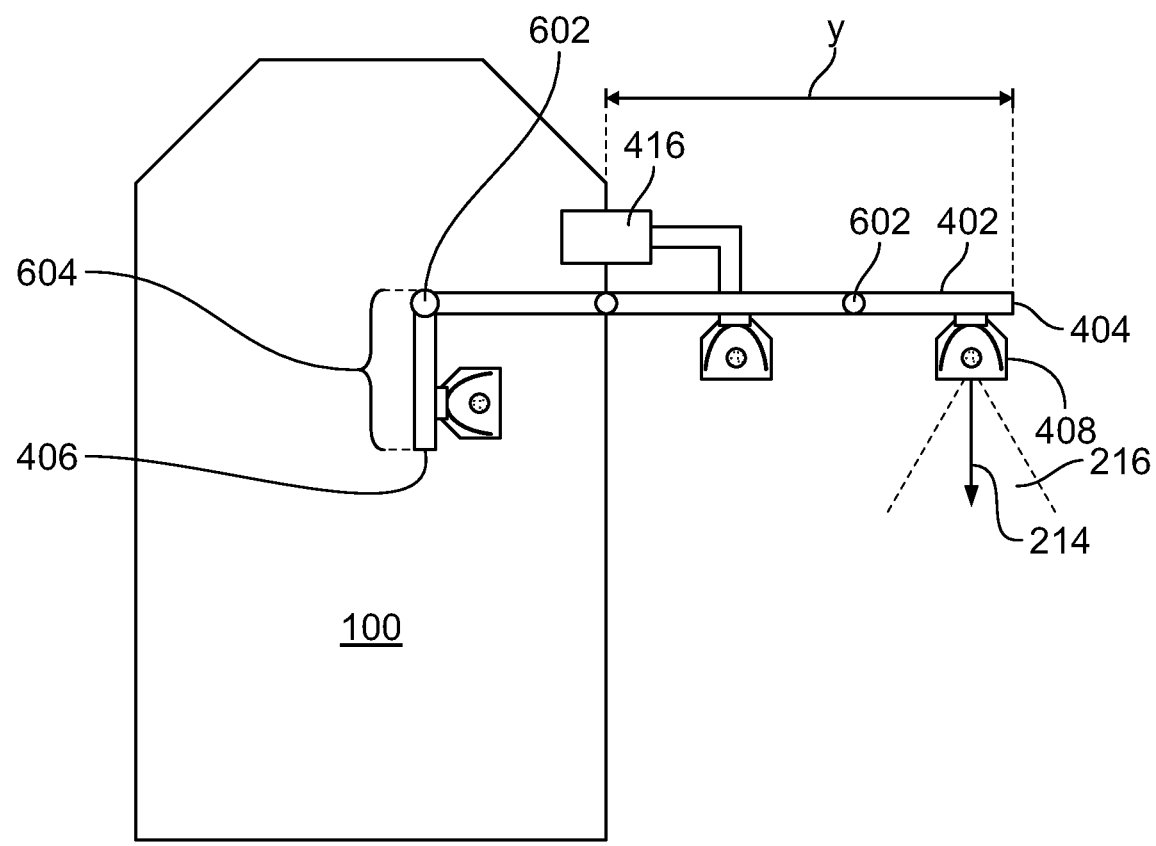
FIG. 6 is a two-dimensional illustration of another variation of a mobile apparatus for ultraviolet (UV) light sanitization of an aircraft, in accordance with exemplary embodiments.

In yet another embodiment, as shown in FIG. 6, the extension arm 402 may have one or more joints 602 that break the extension arm 402 into sections and enable at least a partial folding of the extension arm 402. When present, the combination of the extension actuator 416 and the joints 602 allow for the extension arm to be retracted in the Y direction into the inside of the trolley 100. The retracted sections can fold downward; section 604 is shown folded downward. Using this technique, in embodiments, the entire extension arm 402 could be retracted inside the trolley 100, for example, for storage, or to operate as described in connection with FIGS. 2-3.

Figure 10:
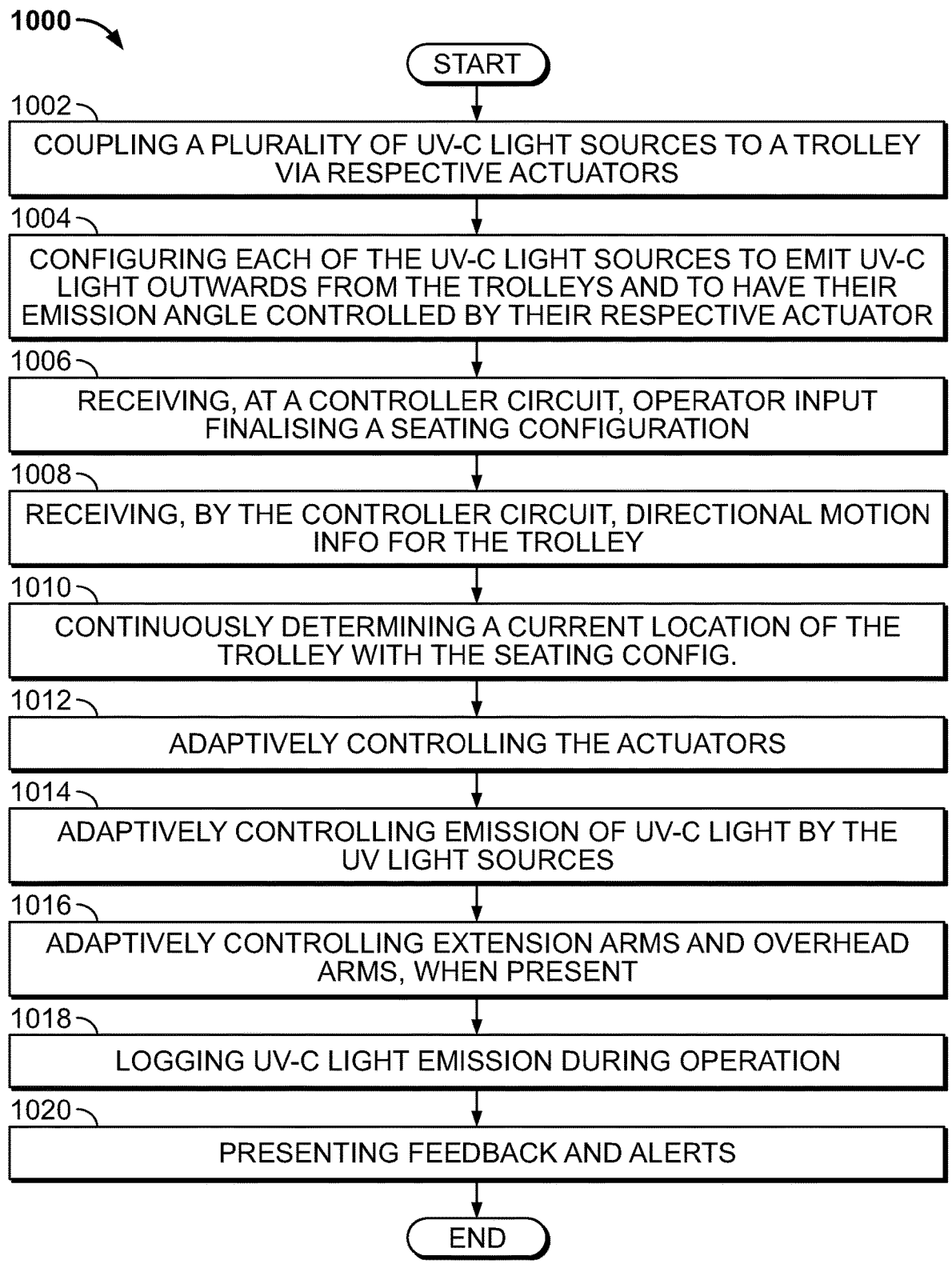
FIG. 10 is a flow chart for a method associated with a mobile apparatus for ultraviolet (UV) light sanitization of an aircraft, in accordance with herein described embodiments.

Referring now to FIG. 10 and with continued reference to FIGS. 1-9, a flow chart is provided for a method 1000 for the mobile apparatus 102, in accordance with various exemplary embodiments. For illustrative purposes, the following description of method 1000 may refer to elements mentioned above in connection with FIGS. 1-9. In practice, portions of method 1000 may be performed by different components of the described system. It should be appreciated that method 1000 may include any number of additional or alternative tasks, the tasks shown in FIG. 10 need not be performed in the illustrated order, and method 1000 may be incorporated into a more comprehensive procedure or method having additional functionality not described in detail herein. Moreover, one or more of the tasks shown in FIG. 10 could be omitted from an embodiment of the method 1000 if the intended overall functionality remains intact.

Before operation, the controller circuit 104 is initialized. As mentioned above, initialization may comprise uploading or updating instructions and applications, program 54, and the like. Initialization at may also include identifying dosimeters 122 and/or external signals and the communication protocols to use with each of them.

At 1002, a plurality of UV-C light sources is coupled to a trolley 100 via respective actuators. At 1004, the operation of configuring each of the UV-C light sources to emit UV-C light outward from the trolley and to have an angle of radiation or emission angle controlled by its respective actuator is performed.

At 1006, the controller circuit receives, from the operator, input finalizing a seating configuration. Finalizing the seating configuration may include the user inputting a seating configuration via the user interface 108. In some embodiments, finalizing the seating configuration includes the user entering a type of aircraft or model of aircraft for the current aircraft, and the controller circuit 104 referencing a look-up table or similar function for that model of aircraft, and presenting a suggested seating configuration, which the user may then customize or approve. The seating configuration contains an arrangement of seats, location of aisles and restrooms and other onboard enclosed areas, and associated distances between rows, breadth of a row, etc.

In various embodiments, the mobile apparatus 102, under direction of the controller circuit 104, is configured to: receive from the user interface operator input that includes finalizing a seating configuration for the aircraft that is aircraft-specific. Finalizing a seating configuration for the aircraft that is aircraft-specific can take different forms. In various embodiments, a user may utilize the user interface 108 to identify the aircraft type (e.g., make, model, call number), and when the aircraft type is identified, the mobile apparatus 102 may provide a potential seating configuration (e.g., two seats, an aisle, and two seats, a forward bathroom located at a first location and an aft bathroom located at a second location, and a total number of rows), and prompt the user to confirm the seating configuration. In various embodiments, the user may edit the seating configuration before confirming it. In various embodiments, the user may enter the seating arrangement without first entering an aircraft type or having been provided a potential seating arrangement; this would be appropriate for a custom aircraft, for example. The controller circuit 104 uses the seating configuration to determine aircraft-specific sanitization requirements for the aircraft; in some embodiments, this may include referencing promulgated rules or regulations. In various embodiments, this step may include the controller circuit 104 commanding the actuators 112 to place their respective UV light sources 110 in an initial position and angular orientation that is optimal for the confirmed seating configuration.

The finalized seating configuration may include a designated start point in the aircraft cabin for the mobile apparatus 102. The user may place the mobile apparatus 102 at the designated starting point in the aircraft cabin (such as, at the cockpit of the aircraft, or by a specific door), and begin operating it by moving it through the aircraft cabin. At 1008, directional motion information for the trolley is received, continuously, from the motion sensor 106.

At 1010, a current location of the trolley with respect to the seating configuration, and hence, cabin geometry, is determined, continuously. The controller circuit 104 utilizes the directional motion and the seating configuration to continuously determine a current location of the trolley 100 with respect to the seating configuration. By knowing where the mobile apparatus 102 started, the aircraft-specific seating configuration for the aircraft, and the directional motion, the mobile apparatus 102 can continually determine its current location within the seating configuration. In some embodiments, at 1010, the controller circuit determines when the trolley is approaching an enclosed space such as a bathroom or closet, and generates a message instructing the operator to open the enclosed space.

At 1012, the actuators 112 are adaptively controlled. In various embodiments, the controller circuit 104 determines, continuously, an optimal angular orientation for one or more of the UV light sources 110, as a function of the current location in the aircraft cabin (e.g., along an aisle), and generates a respective one or more actuator commands 111 to continuously optimize the position and angular orientation of each UV light source 110. As may be appreciated, the optimal angular orientation includes a location in three-dimensional space and an angle of emission that is consistent with the UVC emission needs for the specific aircraft cabin for sanitization, such as, per a Specification. While the mobile apparatus 102 is operating, and based on where it is (its current location) within the specific aircraft, the controller circuit 104 is able to adaptively control the actuators of the plurality of UV light sources by generating the actuator commands 111 based on the current location of the trolley 100. Specifically, the controller circuit 104 may generate actuator commands 111 to change an axis 116 of emitted UV light 114 for one or more of the UV light sources 110. For example, the controller circuit 104 may determine, for the specific seating configuration, and for one or more of the UV light sources 110, that it should direct the axis 116 of the emitted UV light 114 downward as the trolley passes through a partition area, and direct the axis 116 of the emitted UV light 114 more horizontally in an open area, such as where seats are farther apart for an exit row.

At 1014, the emission of the UV-C light from the individual UV light sources 110 is adaptively controlled. As described above, the UV light sources 110 may be controlled by on/off signals, voltages, and the like. Also, while the mobile apparatus 102 is operating, and based on its current location within the specific aircraft, the controller circuit 104 can adaptively generate the respective radiation command 109 for each of the plurality of UV light sources 110. For example, the controller circuit 104 may determine, for the specific seating configuration, and for one or more of the UV light sources 110, that it should increase an intensity of the emitted UV light 114 in an area near a bathroom, and return an intensity of the emitted UV light 114 in a remainder of the cabin of the aircraft. At 1014, the controller circuit 104 may also be selecting radiation patterns, intensity of UV-C emissions, and whether to pulse or continuously radiate from each of the UV light sources 110.

In some embodiments, at 1014, the controller circuit 104 receives UV dosing information from at least one dosimeter 122 located external to the trolley; and adaptively generates the respective radiation command for each of the plurality of UV light sources based on the received UV dosing information. A dosimeter measures dose, which is intensity x time. It can do that by integrating the intensity over the period of time that it's exposed to light. The units for dose are energy/area (ex. J/cm2). The dosimeter 122 may be located on a seat, in an overhead compartment area, in a bathroom, or the like. Dosimeters 122 may be affixed or portable.

In other embodiments, the dosimeter 122 may instead be a sensor or a radiometer. As used herein, a sensor detects the amount of light, in watts, incident on it. Since the area of the sensor is also known by the controller circuit 104, it can calculate a measurement of intensity, measured in watts/area. A radiometer is a sensor tailored for light measurement that also includes the associated electronics to calculate intensity from the sensor response. Note that if controller circuit 104 knows intensity and the speed the cart is moving (and therefore time), it can estimate dose.

At 1016, when present, the extension arm(s) 402 and overhead arm(s) 410 are adaptively controlled. Arms are controlled as described in connection with FIGS. 4-6.

At 1018, in some embodiments, the controller circuit 104 logs emitted UVC light, or the UV-C emissions during operation, as follows. In various embodiments, the controller circuit 104 logs the radiation commands 109 used, as a function of the current location of the trolley, to therefrom generate an UV emissions log. In other embodiments, the controller circuit 104 may keep track of both the actuator commands 111 and the radiation commands 109 used, as a function of its current location, to therefrom generate an UV emissions log. These commands (109 and 111) may be used to generate a map of emitted UV light that reflects the sanitization process that is being, or has been, performed. The logged emitted UVC light, or UV emissions log, may be compared to an aircraft-specific UV sanitization specification.

At 1020, feedback is presented in the form of alerts, messages, and reports, as described above. In an example, as mentioned, the indicators could be designated bulbs that light up. In another example, the indicators could be alphanumeric messages on a display device or touch screen. The mobile apparatus 102 may determine that the speed is too fast or too slow in multiple ways.

In an embodiment, a simple speed limit may be part of the aircraft-specific sanitization specification, and too fast or too slow is determined as a comparison to the speed limit.

In some embodiments, the controller circuit 104 is further configured to compare the logged emitted UV light as a function of the current location of the trolley 100 to an aircraft-specific UV specification for the aircraft; generate a UV high alert when the logged emitted UV light exceeds the UV specification by more than an upper threshold; and, generate a UV low alert when the logged emitted UV light is below the UV specification by more than a lower threshold. The visual feedback presented on the user interface 108 may include the UV high alert and the UV low alert. In some embodiments, the UV specification may have the thresholds built in; in that case, the UV high alert is generated when the logged emitted UV light exceeds the UV specification and the UV low alert is generated when the logged emitted UV light is below the UV specification. In some embodiments, there may be a display of a UV normal indicator when the emitted UV light is neither too high nor too low.

After operation 1020, the method 1000 may end.

Thus, a technologically improved solution for aircraft sanitization in the form of a mobile apparatus for ultraviolet (UV) light sanitization of an aircraft has been presented. As is readily appreciated, the above examples of the mobile apparatus 102 are non-limiting.

Those of skill in the art will appreciate that the various illustrative logical blocks, modules, circuits, and algorithm steps described in connection with the embodiments disclosed herein may be implemented as electronic hardware, computer software, or combinations of both. Some of the embodiments and implementations are described above in terms of functional and/or logical block components (or modules) and various processing steps. However, it should be appreciated that such block components (or modules) may be realized by any number of hardware, software, and/or firmware components configured to perform the specified functions. To clearly illustrate the interchangeability of hardware and software, various illustrative components, blocks, modules, circuits, and steps have been described above generally in terms of their functionality. Whether such functionality is implemented as hardware or software depends upon the application and design constraints imposed on the overall system.

Skilled artisans may implement the described functionality in varying ways for each application, but such implementation decisions should not be interpreted as causing a departure from the scope of the present invention. For example, an embodiment of a system or a component may employ various integrated circuit components, e.g., memory elements, digital signal processing elements, logic elements, look-up tables, or the like, which may carry out a variety of functions under the control of one or more microprocessors or other control devices. In addition, those skilled in the art will appreciate that embodiments described herein are merely exemplary implementations.

Further, the various illustrative logical blocks, modules, and circuits described in connection with the embodiments disclosed herein may be implemented or performed with a general-purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of the method or algorithm described in connection with the embodiments disclosed herein may be embodied directly in hardware, in a software module executed by a controller or processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such that the processor can read information from, and write information to, the storage medium. In the alternative, the storage medium may be integral to the processor. The processor and the storage medium may reside in an ASIC.

In this document, relational terms such as first and second, and the like may be used solely to distinguish one entity or action from another entity or action without necessarily requiring or implying any actual such relationship or order between such entities or actions. Numerical ordinals such as "first," "second," "third," etc. simply denote different singles of a plurality and do not imply any order or sequence unless specifically defined by the claim language. The sequence of the text in any of the claims does not imply that process steps must be performed in a temporal or logical order according to such sequence unless it is specifically defined by the language of the claim. When "or" is used herein, it is the logical or mathematical or, also called the "inclusive or." Accordingly, A or B is true for the three cases: A is true, B is true, and, A and B are true. In some cases, the exclusive "or" is constructed with "and;" for example, "one from the set including A and B" is true for the two cases: A is true, and B is true.

Furthermore, depending on the context, words such as "connect" or "coupled to" used in describing a relationship between different elements do not imply that a direct physical connection must be made between these elements. For example, two elements may be connected to each other physically, electronically, logically, or in any other manner, through one or more additional elements.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A mobile apparatus for ultraviolet (UV) light sanitization of an aircraft, comprising:
a trolley, incorporating therewith a controller circuit operationally coupled to a motion sensor configured to detect directional motion of the trolley, and a user interface configured to receive operator input and provide visual feedback;
a plurality of UV light sources, each UV light source configured to emit UV light outward from the trolley responsive to a respective radiation command of a respective plurality of radiation commands, each UV light source mechanically coupled via a respective actuator to the trolley, each actuator configured to affect an angular orientation of its UV light source responsive to a respective actuator command;
the controller circuit configured to:
receive from the user interface operator input that includes finalizing a seating configuration for the aircraft that is aircraft-specific, the seating configuration including an enclosed space;
utilize the directional motion and the seating configuration to continuously determine a current location of the trolley with respect to the seating configuration;
determine an optimal angular orientation of each UV light source of the plurality of UV light sources, as a function of the current location;
adaptively generate the plurality of radiation commands based on the current location, while the mobile apparatus is operated within the aircraft;
determine when the trolley is approaching the enclosed space; and
generate an alert instructing the operator to open the enclosed space.

2. The mobile apparatus of claim 1, wherein determining the optimal angular orientation of each UV light source of the plurality of UV light sources includes generating respective actuator commands.

3. The mobile apparatus of claim 1, wherein the controller circuit is further configured to:
log emitted UV light as a function of the current location of the trolley;
compare the logged emitted UV light as a function of the current location of the trolley to an aircraft-specific UV specification for the aircraft;
generate a UV high alert when the logged emitted UV light exceeds the UV specification by more than an upper threshold;
generate a UV low alert when the logged emitted UV light is below the UV specification by more than a lower threshold; and
present visual feedback on the user interface, the visual feedback including an indicator of when the trolley is moving too fast and an indicator of when the trolley is moving too slow, an indicator for the UV high alert and an indicator for the UV low alert.

4. The mobile apparatus of claim 1, wherein the controller circuit is further configured to reference a predefined radiation pattern to adaptively generate the radiation commands.

5. The mobile apparatus of claim 4, wherein the radiation pattern is one of a plurality of pre-programmed radiation patterns, and wherein the plurality of radiation patterns includes a high, a medium, and a low intensity UV C-spectrum light.

6. The mobile apparatus of claim 4, wherein the radiation pattern further includes pulsing or continuous radiation.

7. The mobile apparatus of claim 1, wherein the controller circuit is further configured to:
receive UV dosing information from at least one dosimeter located external to the trolley; and
adaptively generate the radiation commands further based on the received UV dosing information.

8. The mobile apparatus of claim 1, further comprising:
an extension arm mechanically coupled to the trolley, the extension arm having a proximal end and a distal end, the extension arm comprising at least one extension UV light source installed between the distal end and the proximal end and an extension actuator configured to respond to commands from the controller circuit; and
an overhead arm coupled to the trolley, the overhead arm comprising at least one overhead UV light source and an overhead actuator configured to respond to commands from the controller circuit.

9. The mobile apparatus of claim 1, further comprising:
a communications circuit on the trolley, operationally coupled to the controller circuit and configured to communicate with the operator by generating the visual feedback on the user interface and receiving the operational instructions from the user interface;
the controller circuit further configured to generate operational data and performance metrics, including a comparison of the logged emitted UV light as a function of the current location to the aircraft-specific UV specification for the aircraft; and
the communications circuit further configured to communicate wired or wirelessly with a server external to the trolley, the operational data and performance metrics.

10. The mobile apparatus of claim 1, wherein the UV light source comprises:
a UV C-spectrum (UVC) radiation source; and
a beam shaping element.

11. The mobile apparatus of claim 9, wherein the UVC radiation source is a mercury lamp, and the beam shaping element is a reflector.

12. The mobile apparatus of claim 9, wherein the UVC radiation source comprises a Light Emitting Diode (LED), and the beam shaping element is a reflector.

13. The mobile apparatus of claim 1, wherein an emission angle of each UV light source is a function of the angular orientation of the UV light source and controlled by a respective actuator command.

14. A mobile apparatus for ultraviolet (UV) light sanitization of an aircraft, comprising:
a trolley, incorporating therewith a controller circuit operationally coupled to a motion sensor configured to detect directional motion of the trolley, and a user interface configured to receive operator input and provide visual feedback;
a plurality of UV light sources, each UV light source configured to emit UV light outward from the trolley responsive to a respective radiation command of a respective plurality of radiation commands, each UV light source mechanically coupled via a respective actuator to the trolley, each actuator configured to affect an angular orientation of its UV light source responsive to a respective actuator command;

the controller circuit configured to:
- receive from the user interface operator input that includes finalizing a seating configuration for the aircraft that is aircraft-specific;
- utilize the directional motion and the seating configuration to continuously determine a current location of the trolley with respect to the seating configuration;
- determine an optimal angular orientation of each UV light source of the plurality of UV light sources, as a function of the current location;
- adaptively generate the plurality of radiation commands based on the current location, while the mobile apparatus is operated within the aircraft;
- log emitted UV light as a function of the current location of the trolley;
- compare the logged emitted UV light as a function of the current location of the trolley to an aircraft-specific UV specification for the aircraft;
- generate a UV high alert when the logged emitted UV light exceeds the UV specification by more than an upper threshold;
- generate a UV low alert when the logged emitted UV light is below the UV specification by more than a lower threshold; and
- present visual feedback on the user interface, the visual feedback including an indicator of when the trolley is moving too fast and an indicator of when the trolley is moving too slow, an indicator for the UV high alert and an indicator for the UV low alert.

\* \* \* \* \*